United States Patent [19]
Schroeder, deceased et al.

[11] 4,375,479
[45] Mar. 1, 1983

[54] INDANYL DERIVATIVES AND USE

[75] Inventors: Eberhard Schroeder, deceased, late of Berlin, Fed. Rep. of Germany, by Kirsten and Christian Shroeder, executors; Clemens Rufer, Berlin, Fed. Rep. of Germany

[73] Assignee: Schering Aktiengesellschaft, Berlin and Bergkamen, Fed. Rep. of Germany

[21] Appl. No.: 343,066

[22] Filed: Jan. 27, 1982

[30] Foreign Application Priority Data

Jan. 27, 1981 [DE] Fed. Rep. of Germany ....... 3103372

[51] Int. Cl.³ .................... A61K 31/18; C07C 143/75
[52] U.S. Cl. .................................... 424/321; 564/82; 564/99
[58] Field of Search .................... 564/82, 99; 424/321

[56] References Cited
U.S. PATENT DOCUMENTS 4,244,960  1/1981  Schröder et al. .................. 546/293

Primary Examiner—Natalie Trousof
Assistant Examiner—Patricia M. Scott
Attorney, Agent, or Firm—Millen & White

[57] ABSTRACT

Compounds of the formula

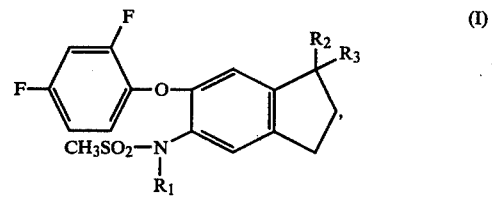

wherein
  $R_1$ is hydrogen, methanesulfonyl, or acetyl,
  $R_2$ and $R_3$ jointly mean oxo, oximino, or separately two hydrogen atoms, or
  $R_2$ is hydrogen and $R_3$ is hydroxy or amino, and when $R_3$ is amino, the physiologically acceptable acid salts thereof possess valuable pharmacological properties.

12 Claims, No Drawings

INDANYL DERIVATIVES AND USE

The present invention concerns novel indanyl derivatives, a process for their preparation and pharmaceutical preparations containing them as active ingredients.

SUMMARY OF THE INVENTION

It is an object of this invention to provide new compounds having valuable pharmacological properties.

Upon further study of the specification and appended claims, further objects and advantages of this invention will become apparent to those skilled in the art.

These objects have been achieved by providing indanyl derivatives of Formula I

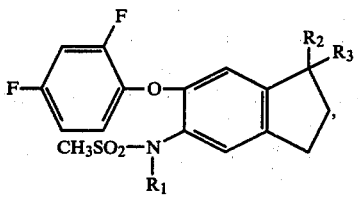

wherein
$R_1$ is hydrogen, methanesulfonyl, or acetyl,
$R_2$ and $R_3$ jointly mean oxo, oximino, or separately two hydrogen atoms, or
$R_2$ is hydrogen and $R_3$ is hydroxy or amino, and when $R_3$ is amino, the physiologically acceptable acid salts thereof.

DETAILED DESCRIPTION

Suitable physiologically acceptable acids for preparing the physiologically acceptable salts include hydrochloric acid, hydrobromic acid, sulfuric acid, phosphoric acid, oxalic acid, malonic acid, tartaric acid and citric acid.

The process of this invention for preparing the novel indanyl derivatives of this invention can be conducted conventionally, e.g., under the conditions set forth in the U.S. Pat. No. 4,244,960 whose disclosure is incorporated by reference herein.

For example, the indanyl derivatives of this invention can be prepared in a conventional manner by condensing a compound of Formula II

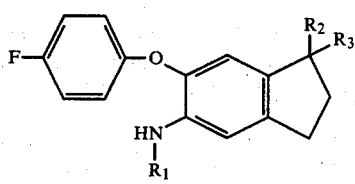

wherein $R_1$, $R_2$, and $R_3$ are as defined above, with methanesulfonic acid chloride, and optionally reducing indanyl derivatives wherein $R_2$ and $R_3$ represent an oxo group or an oximino group, or acetylating indanyl derivatives of Formula I wherein $R_1$ is hydrogen.

The compounds of Formula II are preparable by conventional process disclosed in U.S. Pat. No. 4,244,960.

As compared with the indanyl derivatives described in European Application 9544 (except for the compounds of Formula I wherein $R_2$ and $R_3$ are oximino which are preferably employed as intermediates for preparation of other compounds of this invention), the compounds of this invention are distinguished by superior anti-inflammatory efficacy, as demonstrated by the results of the adjuvant arthritis test described below:

Female and male rats of the Lewis (LEW) strain in a weight span between 110 and 190 g were utilized. The animals received drinking water and "Altromin" pressed feed ad libitum.

Ten rats were used for each dosage group.

Mycobacterium butyricum by Difco, Detroit, was used as the irritant. A suspension of 0.5 mg of Mycobacterium butyricum in 0.1 ml of thinly fluid paraffin (DAB [German Pharmacopoeia]7) was injected in a subplantar fashion into the right hind paw.

The test compounds were administered orally and daily over 4 days starting with the 11th day of the trial. The compounds were given as a clear aqueous solution or crystalline suspension with the addition of "Myrj" 53 (85 mg-%) in an isotonic sodium chloride solution.

The rats were subdivided into various groups as uniformly as possible regarding their body weights. After plethysmographic volume measurement of the right hind paw, 0.1 ml of adjuvant was injected in a subplantar manner into this hind paw.

The right hind paws were measured starting from the 14th day of the trial until the end of the experiment. The duration of the trial was three weeks.

The healing of the right paw of the animal was determined in dependence on the dose of test compound applied.

The Table set forth below demonstrates the results obtained in this test with compounds 3 through 5 of this invention as compared with the structurally analogous indanyl derivatives 1 and 2 previously known from U.S. Pat. No. 4,244,960 which corresponds to the European Patent Application No. 0 009 554. The results show that the compounds of this invention are of good efficacy at doses which are so low that the comparison compounds show practically no efficacy at all at them.

| No. | Compound | Compound mg/kg Animal | % Healing of Right Paw |
|---|---|---|---|
| 1 | N—[6-(4-Fluorophenoxy)-5-indanyl]-methanesulfonamide | 4 × 0.1 | 0 |
|   |   | 4 × 0.3 | 0 |
| 2 | N—[6-(2,4-Dichlorophenoxy)-5-indanyl]methanesulfonamide | 4 × 0.1 | 0 |
|   |   | 4 × 0.3 | 3 |
| 3 | N—[6-(2,4-Difluorophenoxy)-5-indanyl]methanesulfonamide | 4 × 0.1 | 33 |
|   |   | 4 × 0.3 | 40 |
| 4 | N—Acetyl-N—[6-(2,4-difluorophenoxy)-5-indanyl]methanesulfonamide | 4 × 0.1 | 28 |
|   |   | 4 × 0.3 | 38 |
| 5 | 6-(2,4-Difluorophenoxy)-5-methylsulfonyl-1-indanone | 4 × 0.1 | 36 |
|   |   | 4 × 0.3 | 42 |

Accordingly, the novel compounds of this invention are suitable in combination with carriers customary in galenic pharmacy for the treatment of diseases of the spectrum of rheumatic disorders (such as ostearthritis or ankylosing spondylitis), bronchial asthma, hay fever, and others.

It is furthermore remarkable that the indanyl derivatives of this invention are also suitable for the treatment of migraine and dysmenorrhea and reduce the risk of thrombosis.

There may also be compounds among the indanyl derivatives of this invention which may possess, in addition to the antiinflammatory efficacy, a pronounced antiulcerogenic as well as tumor-inhibiting effectiveness.

The useful medicinal preparations (pharmaceutical compositions) are produced in fully conventional fashion by converting the active agents with suitable additives, vehicles, and e.g., flavor-ameliorating agents into the desired forms of administration, such as tablets, dragees, capsules, solutions, inhalants, etc.

For oral administration, tablets, dragees, and capsules are especially well suited, containing, for example, 1-250 mg of active ingredient and 50 mg to 2 g of a pharmacologically inert vehicle, such as, for example, lactose, amylose, talc, gelatin, magnesium stearate, and similar materials, as well as the customary additives.

The typical daily dosage for administration an antiinflammatory is 2-200 mg/kg/day for mammals, including humans. The compounds can be administered for such purposes by analogy to the conventional agent indometacine e.g., by considering the normal factors such as differential potency using fully conventional protocols.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

(a) 10.1 g of 5-bromo-6-nitroindan, 4.1 g of copper(I) chloride, 7.1 g of potassium tert.-butanolate, and 8.5 g of 2,4-difluorophenol were refluxed in 210 ml of tert.-butanol for 7 hours. After cooling, dilution with ether, filtration, concentration, taking up the residue in ether, washing of the ether solution with 1N hydrochloric acid, as well as drying and concentration, 10.5 g of a crude product was obtained which was chromatographed over a silica gel column with hexane-ethyl acetate. Yield: 6.3 g of 5-(2,4-difluorophenoxy)-6-nitroindan, mp 65°-68° C. (from hexane).

(b) 14.6 g of 5-(2,4-difluorophenoxy)-6-nitroindan was combined in 300 ml of dioxane-ether 1:1 with 10 g of Raney nickel and thereafter at 40° C. with 4.86 of hydrazine hydrate. After another 30 minutes at 50° C. and 30 minutes under reflux, the mixture was cooled, filtered, and concentrated. Yield: 13 g of crude 6-(2,4-difluorophenoxy)-5-indanylamine.

(c) At 0° C., 13.1 g of 6-(2,4-difluorophenoxy)-5-indanylamine in 60 ml of pyridine was combined with 4.0 ml of methanesulfonyl chloride. After 3 hours at 0° C. and 16 hours at 20° C., the mixture was concentrated, the residue was taken up in chloroform, the solution was washed with 1N hydrochloric acid, and concentrated. Recrystallization of the residue from ethanol yielded 8.1 g of N-[6-(2,4-difluorophenoxy)-5-indanyl]-methanesulfonamide, mp 85°-87° C.

EXAMPLE 2

3 g of N-[6-(2,4-difluorophenoxy)-5-indanyl]-methanesulfonamide in 30 ml of pyridine was combined at 0° C. within 10 minutes under nitrogen with 1.5 ml of acetic anhydride and stirred for 3 hours at 0° C. and for 13 hours at room temperature. The mixture was concentrated, the residue taken up in chloroform, extracted three times with 1 N hydrochloric acid and once with water, the organic phase was dried over calcium sulfate, concentrated, and the residue was recrystallized from ethanol.

Yield: 3.1 g of N-acetyl-N-[6-(2,4-difluorophenoxy)-5-indanyl]methanesulfonamide, mp 160° C.

EXAMPLE 3

12.8 g of 5-amino-6-(2,4-difluorophenoxy)-1-indanone in 95 ml of pyridine was combined at 0° C. with 8.3 ml of methanesulfonyl chloride. After 3 hours at 0° C. and 16 hours at 20° C., the mixture was concentrated, the residue taken up in chloroform, the solution washed with 1 N hydrochloric acid, and concentrated. Chromatography of the residue over silica gel with dichloromethane-ethyl acetate yielded 1.2 g of 6-(2,4-difluorophenoxy)-5-bis(methylsulfonyl)amino-1-indanone, mp 190° C. (from toluene) and subsequently 8.9 g of 6-(2,4-difluorophenoxy)-5-methylsulfonylamino-1-indanone, mp 153° C. (from ethanol).

The starting compound for this synthesis step can be obtained in two ways:

Method 1

(a) 13.9 g of 6-(2,4-difluorophenoxy)-5-indanylamine in 93 ml of acetic acid was combined at 30° C. with 40 ml of acetic anhydride. Thereafter a solution of 11 g of chromium trioxide in 27 ml of water and 17 ml of acetic acid was added dropwise at 50° C. After another 40 minutes at 50° C., the mixture was cooled, poured on ice water, and vacuum-filtered. The residue was chromatographed over silica gel with dichloromethane-ethyl acetate, thus obtaining 9 g of 5-acetylamino-6-(2,4-difluorophenoxy)-1-indanone, mp 153° C., and subsequently 4 g of the isomeric 6-acetylamino-5-(2,4-difluorophenoxy)-1-indanone, mp 199° C.

(b) 12.9 g of 5-acetylamino-6-(2,4-difluorophenoxy)-1-indanone was refluxed in 210 ml of ethanol with 22 ml of concentrated hydrochloric acid for 2 hours. The mixture was then concentrated, the residue was combined with water and ammonia solution (pH 8), and the solid 5-amino-6-(2,4-difluorophenoxy)-1-indanone was vacuum-filtered. Yield: 11.1 g, mp 132° C.

Method 2

(a) 4.58 g of 5-(2,4-difluorophenoxy)-6-nitroindan and 8.2 g of bis(dimethylamino)tert.-butoxymethane were stirred in 5 ml of dimethylformamide for 60 minutes at 140° C. Concentration under vacuum yielded crude 1-dimethylaminomethylene-5-(2,4-difluorophenoxy)-6-nitroindan.

(b) This product was dissolved in chloroform, and ozone was introduced at −40° C. (12 minutes, rate: 4.5 g per hour). After nitrogen purging, the mixture was poured on ice water, brought to pH 3 with hydrochloric acid, washed with sodium bisulfite solution, and concentrated. Chromatography of the residue over silica gel with chloroform produced 250 mg of 5-(2,4-difluorophenoxy)-6-nitro-1-indanone, mp 145° C. (from ethanol).

(c) This product was dissolved in 5 ml of ethanol-dioxane 1:1, 250 mg of Raney nickel was added thereto and the mixture was then combined at 45° C. with 100 mg of hydrazine hydrate. After 30 minutes of refluxing the mixture was cooled, filtered, and concentrated. Yield: 240 mg of 5-amino-6-(2,4-difluorophenoxy)-1-indanone, mp 153° C. (from ethanol).

EXAMPLE 4

2.82 g of 6-(2,4-difluorophenoxy)-5-methylsulfonylamino-1-indanone was combined in 30 ml of pyridine with 1.57 g of acetyl chloride. After 20 hours at 20° C., the mixture was concentrated, combined with water, brought to pH 6 with hydrochloric acid, and extracted with chloroform. The chloroform extract was washed neutral, concentrated, and the residue chromatographed over silica gel with toluene-ethanol 99:1.

Yield: 2.50 g of 5-(N-acetyl-N-methylsulfonylamino)-6-(2,4-difluorophenoxy)-1-indanone, mp 182° C. (from ethanol).

EXAMPLE 5

3.53 g of 6-(2,4-difluorophenoxy)-5-methylsulfonylamino-1-indanone was dissolved in 35 ml of methanol and 10 ml of 1 N sodium hydroxide solution and, at 5° C., combined in incremental portions with 0.8 g of sodium borohydride. After 16 hours at 20° C., the mixture was concentrated, mixed with 40 ml of water and 26 ml of 1 N hydrochloric acid, and vacuum-filtered. Recrystallization from ethanol yielded 3.07 g of N-[6-(2,4-difluorophenoxy)-1-hydroxy-5-indanyl]methanesulfonamide, mp 127° C.

EXAMPLE 6

7.06 g of 6-(2,4-difluorophenoxy)-5-methanesulfonylamino-1-indanone was refluxed in 100 ml of methanol and 40 ml of water with 3.40 g of sodium acetate trihydrate and 4 g of hydroxylaminohydrochloride for 3 hours. After cooling, the mixture was vacuum-filtered and dried. Yield: 6.16 g of N-[1-hydroxyimino-6-(2,4-difluorophenoxy)-5-indanyl]methanesulfonamide, mp 240° C.

EXAMPLE 7

3.68 g of N-[1-hydroxyimino-6-(2,4-difluorophenoxy)-5-indanyl]methanesulfonamide was dissolved in 100 ml of ethanol. The solution was saturated with gaseous ammonia, 1 g of Raney nickel was added, and hydrogenation was carried out at 90° C. Cooling, filtering, concentrating, combining with ethanolic hydrochloric acid, concentrating, and crystallizing with ether yielded 2.99 g of N-[1-amino-6-(2,4-difluorophenoxy)-5-indanyl]methanesulfonamide, hydrochloride, mp 220° C.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. An indanyl derivative of the formula

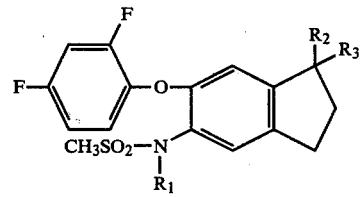

wherein
$R_1$ is hydrogen, methylsulfonyl, or acetyl,
$R_2$ and $R_3$ jointly are oxo or oximino, or separately each is hydrogen, or
$R_2$ is hydrogen and $R_3$ is hydroxy or amino, or, when $R_3$ is amino, a physiologically acceptable salt thereof with an acid.

2. N-[6-(2,4-Difluorophenoxy)-5-indanyl]methanesulfonamide, a compound of claim 1.

3. N-Acetyl-N-[6-(2,4-difluorophenoxy)-5-indanyl]methanesulfonamide, a compound of claim 1.

4. 6-(2,4-Difluorophenoxy)-5-methylsulfonylamino-1-indanone, a compound of claim 1.

5. 5-(N-Acetyl-N-methylsulfonylamino)-6-2,4-difluorophenoxy)-1-indanone, a compound of claim 1.

6. N-[6-(2,4-Difluorophenoxy)-1-hydroxy-5-indanyl]methanesulfonamide, a compound of claim 1.

7. N-[1-Amino-6-(2,4-difluorophenoxy)-1-indanyl]methanesulfonamide hydrochloride, a compound of claim 1.

8. A compound of claim 1 wherein $R_1$ is H or acetyl.

9. A compound of claim 1 wherein $R_2$ and $R_3$ are hydrogen.

10. A pharmaceutical composition comprising an amount of a compound of claim 1 effective as an antiinflammatory and a pharmaceutically acceptable carrier.

11. A pharmaceutical composition comprising an amount of two compounds of claim 1 effective as an antiinflammatory and a pharmaceutically acceptable carrier.

12. A method of treating inflammation in a patient in need of such treatment comprising administering an antiinflammatory amount of a compound of claim 1.

* * * * *